United States Patent [19]

Rossetti et al.

[11] 4,165,317
[45] Aug. 21, 1979

[54] RIFAMYCIN COMPOUNDS

[75] Inventors: Vittorio Rossetti; Leonardo Marsili; Carmine Pasqualucci, all of Milan, Italy

[73] Assignee: Archifar Laboratori Chimico Farmacologici S.p.A., Rovereto, Italy

[21] Appl. No.: 825,166

[22] Filed: Aug. 12, 1977

[30] Foreign Application Priority Data

Sep. 30, 1976 [IT] Italy ................................ 5209 A/76

[51] Int. Cl.$^2$ ........................................... C07D 498/18
[52] U.S. Cl. .......................... 260/239.3 P; 424/273 R
[58] Field of Search ................................. 260/239.3 P

[56] References Cited

FOREIGN PATENT DOCUMENTS 1670479 1/1971 Fed. Rep. of Germany .... 260/239.3 P
1670377 2/1974 Fed. Rep. of Germany .... 260/239.3 P
2622638 12/1976 Fed. Rep. of Germany .... 260/239.3 P

*Primary Examiner*—John M. Ford
*Assistant Examiner*—Robert T. Bond
*Attorney, Agent, or Firm*—Haseltine, Lake & Waters

[57] ABSTRACT

Rifamycin compounds having high antibacterial activity, comprising powder of yellow-orange color.

Such compounds are obtained by reacting 3-aminosubstituted-4-desoxo-4-imino rifamycin S with aldehydes of formula X—CHO.

1 Claim, No Drawings

RIFAMYCIN COMPOUNDS

This invention relates to novel rifamycin compounds having antibacterial activity.

In German Patent Application DOS 1,670,479 laid open on Jan. 28, 1971 and in German Pat. No. 1,670,377 derivatives granted on Feb. 28, 1974 of rifamycin S are described as having the formula:

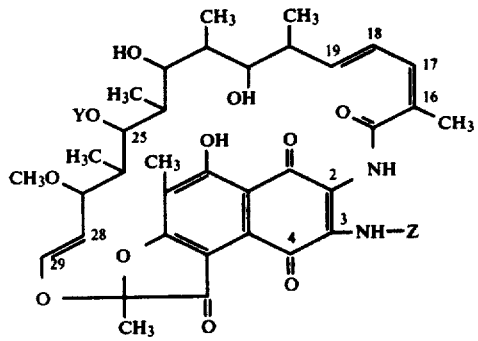

and 16, 17, 18, 19 tetrahydroderivatives and 16, 17, 18, 19, 28, 29 hexahydroderivatives thereof, wherein:

Y is —H or —COCH$_3$, and

Z is inter alia an alkyl having 1–4 carbon atoms; cycloalkyl having 3–6 carbon atoms; phenyl; phenyl substituted with at least one radical selected from the group consisting of halogen, methyl and hydroxy.

The present applicants have synthesized rifamycin compounds having the formula

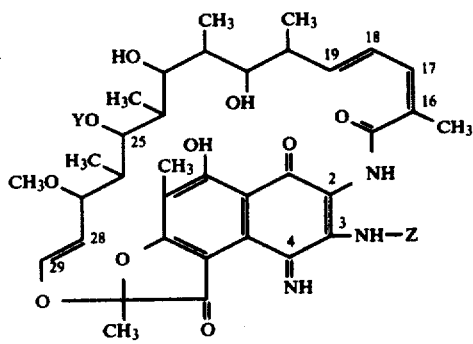

and 16, 17, 18, 19 tetrahydroderivatives and 16, 17, 18, 19, 28, 29 hexahydroderivatives thereof, wherein Y and Z are as those above defined.

These compounds of formula (II) are obtained by dissolving in a solvent selected from the group consisting of tetrahydrofuran and 1,4-dioxane a compound of formula (I), and reacting said a solution with ammonia gas at a temperature between −10° C. and +35° C. for a time in the range of 1–40 hours.

This invention relates to rifamycin compounds having the formula:

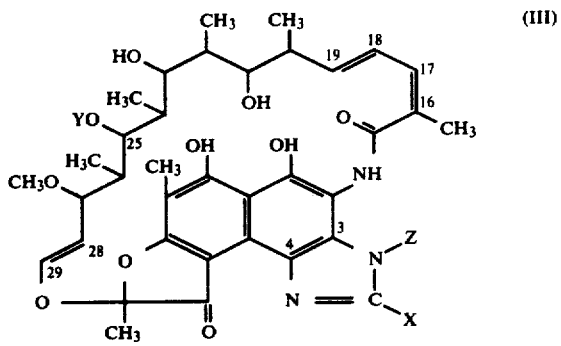

and 16, 17, 18, 19 tetrahydroderivatives and 16, 17, 18, 19, 28, 29 hexahydroderivatives thereof, wherein Y and Z are those as defined as in formula II, above and X is selected from the group consisting of hydrogen, an alkyl having 1-5 carbon atoms, carboxyl, formyl, phenyl, arylalkenyl hydrocarbon having 8 carbon atoms, cycloalkyl having 6 carbon atoms, cycloalkenyl having 6 carbon atoms, alkenyl having 3 carbon atoms, 5-member heterocyclo having one heteroatom selected from the group consisting of N, O and S, 6-member heterocyclo having one heteroatom selected from the group consisting of N and O, and substitution products of the above specified radicals having at least one radical different therefrom and selected from the group consisting of halogen, methyl, methoxyl, N,N-dimethylamino and carboxyl.

These compounds have high antibacterial activity on Gram-positive and Gram-negative bacteria and particularly on Mycobacterium Tuberculosis. Such compounds are powders of yellow-orange colour, soluble in most of the organic solvents, such as chlorinated solvents, alcohols, esters, ethers, and partially soluble in aromatic hydrocarbons.

The compounds of formula (III) are obtained by dissolving a compound of formula (II) in an aprotic solvent selected from the group consisting of tetrahydrofuran, 1,4-dioxane and dimethyl sulphoxide, and reacting it at a temperature of 10°–60° C. for a time in the range of 2–30 hours with an aldehyde having the formula:

X—CHO wherein X is that as specified for the compounds of formula (III), the reaction being carried out in the presence of a reducing metal selected from the group consisting of Zn and Fe, and in the presence of an organic acid selected from the group consisting of formic acid and acetic acid. Since, as set forth above, the compound of formula (II) is obtained from the compound of formula (I), the compound of formula (III) can be directly obtained from the compound of formula (I) without isolating the compound of formula (II).

Compounds of formulae similar to that of the compounds according to the present invention are described in German Patent Applications DOS 2,622,638 laid open on Dec. 9, 1976 and DOS 2,626,296 laid open on Dec. 30, 1976, but are distinguished therefrom in that the C atoms in positions 3 and 4 are bonded to one another in a ring by the group

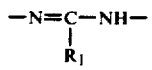

and respectively in that the C atoms in position 3,4 are bonded to one another in a ring by

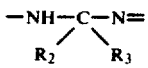

In order that the invention be more clearly understood, some exemplary embodiments of the invention will now be described, as given by way of not limitation. In the examples, the chromatographies on thin layer have been made on silica gel plates Merck $F_{254}$ 5×10 cm, using a mixture benzene/ethyl acetate/methanol (20:7:8) as eluent.

I.R. spectra have been made in vaseline oil suspension (Nujol).

Electronic absorption spectra have been made in methanol suspension.

EXAMPLE 1

In a solution of 5 g 3-(m-toluidino)-rifamycin S in 50 ml tetrahydrofuran, ammonia gas was bubbled at 5° C. for 5 minutes. The reaction mixture was allowed to stand at room temperature for 2 hours. After vacuum removal of excess ammonia, 5 g glioxylic acid and 2 g powder zinc were added under stirring, then 20 ml acetic acid were dropwise added, maintaining the temperature at 5° C. Stirring was continued at room temperature for 2 hours, then the mixture was filtered and dropped in 300 ml water. The mixture was filtered again and neutralized with sodium bicarbonate, then adding 100 ml chloroform and stirring for 5 minutes. A yellow solid was separated, filtered and washed with chloroform. Yield: 2.1 g product of formula (III), wherein X is carboxyl and Z is 3-tolyl.

I.R. 3450, 3370, 3210, 3080, 1731, 1691, 1660, 1595(B), 1400(Sh), 1340, 1303, 1250(B), 1158, 1126, 1109, 1068, 1023, 980, 950, 937, 920, 887, 845, 810, 795 and 764 cm$^{-1}$.

Rf=0.52

$\lambda_{max}$=412 nm ($E_1$ $_{cm}$$^{1\%}$=194.8).

EXAMPLE 2

In a solution of 5 g 3-anilino-rifamycin S in 50 ml tetrahydrofuran ammonia gas was bubbled at 0° C. for 5 minutes. The reaction mixture was allowed to stand overnight at room temperature. After vacuum removal of excess ammonia, 5 g 4-dimethylamino benzaldehyde and 2 g powder zinc were added under stirring and 20 ml acetic acid were dropwise added, maintaining the temperature at 8° C. Stirring was continued for one hour at room temperature, the unreacted zinc was filtered and 50 ml chloroform were added. After washing three times with water, the organic layer was separated and dried on sodium sulphate. The product was vacuum concentrated and chromatographied on column filled up with 250 g silica gel, eluting with benzene/acetone (75:25).

Yield: 0.8 g red solid product of formula (III), wherein X is 4-dimethylamino phenyl and Z is phenyl.

I.R. 3400(B), 1710(B), 1658(Sh), 1608, 1573, 1535, 1345, 1320, 1285, 1261, 1238, 1195, 1175, 1066, 1020, 977, 948, 923, 896, 824, 806 and 754 cm$^{-1}$.

Rf=0.67

$\lambda_{max}$=432 nm ($E_1$ $_{cm}$$^{1\%}$=153).

EXAMPLE 3

In a solution of 3 g 3-propylamino-rifamycin S in 30 ml tetrahydrofuran, ammonia gas was bubbled at 2° C. for 5 days. The reaction mixture was allowed to stand overnight at 5° C. After vacuum removal of excess ammonia, 3 g benzaldehyde and 2 g powder zinc were added under stirring, then dropwise adding 10 ml acetic acid at 10° C. Stirring was continued for one hour at room temperature, the unreacted zinc was filtered, 50 ml chloroform were added, then washing with 15% aqueous solution of sodium sulphite. The organic layer was dried on sodium sulphate, and evaporating at reduced pressure and chromatographying on column filled up with silica gel, eluting with benzene/acetone (80:20). A residue was obtained, that crystallized from toluene yielded 0.5 g yellow crystalline product of formula (III), wherein X is phenyl and Z is propyl.

I.R. 3400(B), 1735, 1720, 1655, 1595, 1490, 1345, 1235, 1160, 1060, 1020, 970, 920, 940, 890, 880 and 805 cm$^{-1}$.

Rf=0.55

$\lambda_{max}$=257 nm ($E_1$ $_{cm}$$^{1\%}$=327), 306 nm ($E_1$ $_{cm}$$^{1\%}$=337), 359 nm ($E_1$ $_{cm}$$^{1\%}$=94), 421 nm ($E_1$ $_{cm}$$^{1\%}$=154).

EXAMPLE 4

In a soluzion of 5 g 3-anilino-rifamycin S in 50 ml tetrahydrofuran, ammonia gas was bubbled at 3° C. for 8 minutes. The reaction mixture was allowed to stand overnight at 6° C. After vacuum removal of excess ammonia, 5 g cinnamaldehyde and 2 g powder zinc were added under stirring, then dropwise adding 20 ml acetic acid at 9° C. Stirring was continued at room temperature for 30 minutes, the unreacted zinc was filtered, the product was diluted with 50 ml chloroform and washed for three times with 15% aqueous solution of sodium sulphite. As dried on sodium sulphate, the organic layer was concentrated to small volume at reduced pressure and the product was chromatographied on column filled up with silica gel, eluting with benzene/acetone (75:25). After evaporation of suitable eluate fractions, a solid crumbling in isopropyl ether was obtained. Yield: 1.6 g red product of formula (III), wherein X is styryl and Z is phenyl.

I.R. 3400, 1720(B), 1655, 1630, 1595, 1495, 1345, 1241, 1165, 1091, 1065, 1023, 970, 945(Sh), 897, 855, 809, 760 and 705 cm$^{-1}$.

Rf=0.67

EXAMPLE 5

In a solution of 5 g 3-(ortho-toluidino)-rifamycin S in 50 ml tetrahydrofuran, ammonia gas was bubbled for 5 minutes at 0° C. The reaction mixture was allowed to stand for 4 hours at 10° C. After vacuum removal of excess ammonia, 5 g benzaldehyde and 2 g powder zinc were added under stirring, then dropwise adding 20 ml acetic acid at 7° C. Stirring was continued for 1 hour at room temperature, the unreacted zinc was filtered, then the product was dropped in 30 ml water containing 5 g sodium sulphite, then diluting with 50 ml chloroform and washing with water. The organic layer was dried on sodium sulphate and the product evaporated to dryness at reduced pressure. Crystallizing from tetrahydrofuran, a yellow crystalline product of formula (III) was obtained, wherein X is phenyl and Z is 2-tolyl.

I.R. 3490, 3420, 3380, 1720, 1660, 1640, 1593, 1560, 1425, 1345, 1315, 1260, 1243, 1215(Sh), 1172, 1125, 1095, 1071, 1025, 986, 974, 950, 925, 900, 860, 815, 777, 735 and 706 cm$^{-1}$.

Rf=0.60

$\lambda_{max}$=421 nm (E$_{1\ cm}$$^{1\%}$=148.9).

EXAMPLE 6

In a solution of 5 g 3-(m-chloroanilino)-rifamycin S in 50 ml tetrahydrofuran, ammonia gas was bubbled at 3° C. for 5 minutes. The reaction mixture was allowed to stand at room temperature for 3½ hours. After vacuum removal of excess ammonia, 5 g crotonaldehyde and 2 g powder zinc were added under stirring, then dropwise adding 20 ml acetic acid at 8° C. The reaction mixture was stirred for 30 minutes at 15° C. and the unreacted zinc was filtered, then adding 30 ml water containing 5 g sodium sulphite, diluting with 50 ml chloroform and repeatedly washing with water. As dried on sodium sulphate, the organic layer was concentrated to small volume at reduce pressure and the product chromatographied on column filled up with 250 g silica gel, eluting with benzene/acetone (8:2). 0.8 g yellow crystalline product of formula (III) were obtained, wherein X is 2-propen-3-il and Z is 3-chloro-phenyl.

I.R. 3400(B), 1740-1715, 1660(B), 1596, 1350, 1310, 1250, 1169, 1068, 1025, 980, 955, 900, 870, 810 and 768 cm$^{-1}$.

Rf=0.63

$\lambda_{max}$=418 nm (E$_{1\ cm}$$^{1\%}$=129).

EXAMPLE 7

In a solution of 5 g 3-anilino-rifamycin S in 50 ml tetrahydrofuran, ammonia gas was bubbled at 0° C. for 5 minutes. After rise in temperature to normal room temperature value, the mixture was allowed to stand for 3 hours, excess ammonia was removed under vacuum and 5 g 5-bromo thiophen-2-aldehyde and 2 g powder zinc were added under stirring, then dropwise adding 20 ml acetic acid at 12° C. The reaction mixture was stirred at room temperature for 20 hours. The unreacted zinc was filtered and the product poured into 15% aqueous solution of sodium sulphite, then stirring with magnetic stirrer for 10 minutes, diluting with 100 ml water and extracting with 50 ml chloroform. As washed with water and dried on sodium sulphate, the organic layer was vacuum concentrated to dryness in a rotary evaporator. The residue was chromatographied on silica gel column, eluting with benzene/acetone (8:2), thus obtaining 1.1 g product of formula (III), wherein X is 5-bromo thiophen-2-yl and Z is phenyl.

I.R. 3400, 3300, 1735, 1718, 1653(B), 1595, 1498, 1345, 1308, 1265, 1245, 1163, 1094, 1070, 1025, 980, 952, 895, 858, 813 and 765 cm$^{-1}$.

Rf=0.63

$\lambda_{max}$=418 nm (E$_{1\ cm}$$^{1\%}$=132.8).

EXAMPLE 8

2.5 g 3-anilino-4-desosso-4-imino-rifamycin S were dissolved in 25 ml tetrahydrofuran, the solution was cooled to 0° C. and 2.5 g glioxylic acid and 1.2 g powder zinc were added, then dropwise adding 10 ml acetic acid under good stirring without exceeding 5° C. Stirring was continued for further 20 minutes at 15° C. and excess zinc was filtered. As diluted with 50 cc water, the filtrate was added with 25 ml chloroform. Immediately, a yellow crystalline solid was separated that filtered, washed with water and dried, yielded 1.1 g product of formula (III), wherein X is carboxyl and Z is phenyl.

I.R. 3450, 3350, 1725, 1695, 1660, 1635, 1595(B), 1295, 1240, 1164, 1125, 1090, 1065, 1048, 1018, 976, 950, 920, 890, 840, 810, 765, 730 and 700 cm$^{-1}$.

Rf=0.55

$\lambda_{max}$=412 nm (E$_{1\ cm}$$^{1\%}$=213).

EXAMPLE 9

In a solution of 5 g 3-anilino-rifamycin S in 50 ml tetrahydrofuran, ammonia gas was bubbled at 0° C. for 5 minutes. The solution was allowed to stand for 2 hours at room temperature, excess ammonia was removed under vacuum, 5 g furfural and 2 g powder zinc were added under stirring, then dropwise adding 20 ml acetic acid at 6° C. The reaction mixture was stirred at 10° C. for 30 minutes; the unreacted zinc was filtered and the solution poured into 30 ml water containing 5 g sodium sulphite, then diluting with 100 ml water and extracting with chloroform. As washed with water, the organic layer was evaporated and charged on column filled up with silica gel. By eluting with benzene/acetone (75:25), 1.2 g yellow crystalline product of formula (III) were obtained, wherein X is 2-furyl and Z is phenyl.

I.R. 3400(B), 1730, 1635, 1590, 1520(Sh), 1499, 1345, 1290, 1251, 1240, 1167, 1125, 1068, 1026, 979, 949, 913, 890, 845, 810 and 765 cm$^{-1}$.

Rf=0.57

$\lambda_{max}$=424 nm (E$_{1\ cm}$$^{1\%}$=135.4).

| Elementary analysis for: C$_{48}$H$_{55}$N$_{3}$O$_{12}$ | | | |
|---|---|---|---|
| | C | H | N |
| Calculated, % | 66.57 | 6.41 | 4.85 |
| Found, % | 66.42 | 6.12 | 4.29 |

EXAMPLE 10

In a solution of 5 g 3-anilino-rifamycin S in 50 ml tetrahydrofuran, ammonia gas was bubbled at 0° C. for 5 minutes. The mixture was allowed to stand at room temperature for 2 hours. Unreacted ammonia was removed under vacuum and 5 g cyclohexanaldehyde and 2 g powder zinc were added under stirring, then dropwise adding 20 ml acetic acid at 6° C. The reaction mixture was stirred at room temperature for 30 minutes. The unreacted zinc was removed by filtering, the filtrate was added to 30 ml water containing 5 g sodium sulphite, then diluting with 100 ml water and extracting with chloroform. After evaporating the solvent at reduced pressure, the residue was chromatographied on silica gel column and, eluting with benzene/acetone (75:25), 1.5 g yellow product of formula (III) were obtained, wherein X is cyclohexyl and Z is phenyl.

I.R. 3400(B), 1715, 1658, 1634, 1595, 1546, 1499, 1345, 1303, 1242, 1165, 1095, 1067, 1025, 976, 950, 894, 875, 810 and 765 cm$^{-1}$.

Rf=0.62

$\lambda_{max}$=414 nm (E$_{1\ cm}$$^{1\%}$=194.3).

EXAMPLE 11

In a solution of 5 g 3-anilino-rifamycin S in 50 ml tetrahydrofuran, ammonia gas was bubbled at 0° C. for 5 minutes. After 2 hours stand at room temperature, excess ammonia was removed under vacuum and 5 g 2,4-dichloro-benzaldehyde and 2 g powder zinc were added, then dropwise adding 20 ml acetic acid at 5° C. Stirring was continued at room temperature for 2 hours and unreacted zinc was filtered. The filtrate was treated with 30 ml water and 5 g sodium sulphite for 5 minutes, then diluting with 50 ml chloroform and repeatedly washing with water. Following solvent evaporation, the residue was purified on column filled up with silica gel and, eluting with benzene/acetone (85:15), a yellow solid was obtained that, crystallized from 20 ml benzene, yielded 1.8 g product of formula (III), wherein X is 2,4-dichlorophenyl and Z is phenyl.

I.R. 3375, 3250, 1720, 1650(B), 1590, 1240, 1160, 1107, 1065, 1025, 975, 948, 895, 845, 810 and 765 cm$^{-1}$.

Rf=0.69

$\lambda_{max}$=414 nm (E$_1$ $_{cm}$$^{1\%}$=119.4)

| Elementary analysis for: C$_{50}$H$_{55}$N$_3$O$_{11}$Cl$_2$ | | | |
|---|---|---|---|
| | C | H | Cl |
| Calculated, % | 63.56 | 5.87 | 7.50 |
| Found, % | 63.73 | 5.57 | 7.55 |

EXAMPLE 12

In a solution of 3-(m-hydroxy-anilino)-rifamycin S in 50 ml tetrahydrofuran, ammonia gas was bubbled at 0° C. for 5 minutes. The mixture was allowed to stand at room temperature for 2 hours and excess ammonia was removed under vacuum. 5 g furfural and 2 g zinc were added under stirring, then dropwise adding 20 ml acetic acid at 5° C. Stirring was continued at room temperature for 2½ hours. After filtering, the obtained solution was whipped with 5 g sodium sulphite dissolved in 30 ml water, then extracting with chloroform and repeatedly washing with water. As dried and evaporated, the organic layer yielded a residue that was purified on silica gel column, eluting with benzene/acetone (7:3). A yellow solid of formula (III) was obtained, wherein X is 2-furyl and Z is 3-hydroxy phenyl, that after crystallization from benzene, was chromatographically pure (0.9 g).

I.R. 3375(B), 1725-1715, 1600(B), 1342, 1240, 1165, 1125, 1065, 1030, 1005, 975, 950, 926, 892, 810 and 770 cm$^{-1}$.

Rf=0.61

$\lambda_{max}$=422 nm (E$_1$ $_{cm}$$^{1\%}$=116.2).

EXAMPLE 13

In a solution of 5 g 3-anilino-rifamycin S in 50 ml tetrahydrofuran, ammonia gas was bubbled at 0° C. for 5 minutes. The mixture was allowed to stand at room temperature for 2 hours and excess ammonia was removed, then adding 5 g trioxymethylene, 2 g powder zinc and dropwise adding 20 ml acetic acid under good stirring and at 5° C. The mixture was overnight stirred at room temperature and filtered. As extracted with chloroform, washed, dried and evaporated, the filtrate yielded 5.6 g residue, that was chromatographied on column and, eluting with benzene/acetone (85:15), 0.9 g product of formula (III) were obtained, wherein X is hydrogen and Z is phenyl.

I.R. 3400(B), 1725, 1660, 1495(Sh), 1340, 1295, 1245, 1165, 1100(B), 1065, 1018, 975, 950, 920, 893, 810 and 770 cm$^{-1}$. M+ 797 (field desorption mass spectrometry) (C$_{44}$H$_{51}$N$_3$O$_{11}$)

$\lambda_{max}$=411 nm (E$_1$ $_{cm}$$^{1\%}$=131.9). Rf=0.54

The $^1$H NMR (CDCl$_3$/DMSO-d$_6$:1/1) displays the following main absorption peaks: -0.37 δ [d,CH$_3$-C(H)], 0.27 δ [d,CH$_3$-C(H)], 0.82 δ [2d, 2CH$_3$-C(H)], 1.60, 1.73, 1.88,

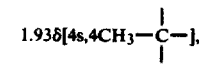

1.93δ[4s,4CH$_3$—C—], 2.90 δ [s, CH$_3$O], 4.7–6.8 δ [m, C-25 and olefinic protons], 7.35 δ [broad, s, C$_6$H$_5$], 9.15 δ [s, CH=N]; the $^{13}$CNMR (DMSO-d$_6$) shows a signal at 136.8 p.p.m. (doublet in the off-resonance spectrum) attributable to the imidazolinic carbon atom (TMS as internal standard).

EXAMPLE 14

In a solution of 5 g 3-anilino-rifamycin S in 50 ml tetrahydrofuran ammonia gas was bubbled at 0° C. for 5 minutes. The mixture was allowed to stand at room temperature for 2 hours, excess ammonia was removed and under stirring 5 g piridin-3-aldehyde and 2 g zinc were added, then slowly dropwise adding 20 ml acetic acid without exceeding 5° C. The mixture was stirred at 10° C. for 30 minutes, filtered, added with 30 ml 15% aqueous solution of sodium sulphite and 50 ml chloroform, then stirring for 5 minutes with magnetic stirrer and filtering again, diluting with 100 ml water and decanting. The organic layer was repeatedly washed with water, anhydrified and evaporated to dryness at reduced pressure.

The residue was chromatographied on silica gel column (eluent benzene/acetone 75:25), obtaining 2.7 g yellow product that crystallized from 27 ml benzene yielded 1 g pure product of formula (III) wherein X is 3-pyridyl and Z is phenyl.

I.R. 3425, 3375, 3250, 1730, 1650, 1632, 1593, 1495(Sh), 1350(Sh), 1245, 1198, 1165, 1125, 1065, 1025, 978, 945, 892, 810, 760 and 710 cm$^{-1}$.

Elementary analysis for: C$_{49}$H$_{56}$N$_4$O$_{11}$. Calculated, % C 67.10 H 6.45. Found, % C 67.01 H 5.89.

$\lambda_{max}$=419 nm (E$_1$ $_{cm}$$^{1\%}$=130). Rf=0.52.

EXAMPLE 15

In a solution of 3 g 3-cyclohexylamino-rifamycin S in 30 ml tetrahydrofuran, ammonia gas was bubbled at 0° C. for 2 days. The mixture was allowed to stand at room temperature for 2 days. Excess ammonia was removed under vacuum and 4 g furfural and 2.2 g powder zinc were added under stirring and then 12 ml acetic acid were dropwise added at 5° C. The mixture was stirred for 36 hours at 20° C. and filtered. The filtrate was treated with 20 ml solution of sodium sulphite, extracted with chloroform and the organic layer was washed with water, anhydrified and vacuum concentrated. The residue was chromatographied on silica gel column, eluting with benzene/acetone (85:15). A mixture was obtained and chromatographied again to yield 600 mg pure product of formula (III), wherein X is 2-furyl and Z is cyclohexyl.

Rf=0.70

$\lambda_{max}$=448.5 nm (E$_1$ $_{cm}$$^{1\%}$=100.9).

EXAMPLE 16

In a solution of 5 g 3-anilino-rifamycin S in 50 ml tetrahydrofuran, ammonia gas was bubbled at 0° C. for 5 minutes. The reaction was continued for 2 hours at 20° C., excess ammonia was removed under vacuum, and 4 g 2-carboxy benzaldehyde, 2 g powder zinc and 20 ml acetic acid were added under stirring. The reaction was continued under stirring at 15° C. for 24 hours, and the mixture was filtered, whipped with 30 ml 15% sodium sulphite for 5 minutes and extracted with chloroform. As washed with water, the organic layer was added with 50 ml aqueous solution of 10% potassium ferricyanide, vigorously stirred for one hour, decanted, washed and anhydrified with sodium sulphate. Following evaporation at reduced pressure, the product was suspended in 100 ml ethyl acetate. The solution was extracted for seven times with 50 ml buffer phosphate at pH 7.4. The buffer extracts were combined, acidified at pH 2.5 with concentrated hydrochloric acid and extracting with 100 ml dichloromethane. After evaporation and crumbling with isopropyl ether, 1.15 g product of formula (III) in the form of yellow crystals were obtained, wherein X is 2-carboxy phenyl and Z is phenyl.

I.R. 3400, 1720, 1665, 1640, 1600(B), 1500, 1343, 1265, 1245, 1160(B), 1130, 1070, 1028, 980, 955, 900, 855, 810, 770, 730 and 705 cm$^{-1}$.

Rf = 0.24

$\lambda_{max} = 415$ nm ($E_1$ $_{cm}$$^{1\%}$ = 154.5).

EXAMPLE 17

In a solution of 5 g 3-(p-chloro-anilino)-rifamycin S in 50 ml tetrahydrofuran, ammonia gas was bubbled at 0° C. for 5 minutes. The mixture was allowed to stand at 5° C. for 24 hours. Excess ammonia was removed under vacuum, then adding under stirring 5 g thiophen-2-aldehyde and 2 g powder zinc, followed by dropwise addition of 20 ml acetic acid at 0° C. The reaction mixture was stirred for 2 hours at 0° C. and filtered. The filtrate was whipped for 5 minutes with 30 ml 15% aqueous solution of sodium sulphite, diluted with 100 ml water and extracted with chloroform. As washed and dried, the organic layer was evaporated to dryness at reduced pressure, obtaining an oil that was purified by percolation in column containing 250 g silica gel, eluting with benzene/acetone (75:25). Thus, an impure product was obtained which, after a second chromatography yielded 0.8 g pure crystalline product of formula (III), wherein X is 2-thienyl and Z is 4-chloro-phenyl.

I.R. 3400, 3275, 1715, 1652, 1595, 1495, 1410, 1345, 1240, 1160, 1095, 1065, 1020, 978, 950, 892, 860 and 810 cm$^{-1}$.

Rf = 0.67

$\lambda_{max} = 420$ nm ($E_1$ $_{cm}$$^{1\%}$ = 130.3).

EXAMPLE 18

In a solution of 5 g 3-anilino-rifamycin S in 50 ml tetrahydrofuran, ammonia gas was bubbled at 0° C. for 5 minutes. The mixture was allowed to stand at room temperature for 2 hours, excess ammonia was removed under vacuum and under stirring 5 g 5-methyl-furfural and 2 g zinc were added, followed by dropwise addition of 20 ml acetic acid at 10° C. The mixture was stirred at room temperature for 24 hours and filtered, and the filtrate was stirred with 30 ml 15% solution of sodium sulphite, diluted with 100 ml water and extracted with chloroform. The organic layer was repeatedly washed, dried and evaporated to dryness under vacuum. The residue was chromatographied on silica gel column (eluent benzene/acetone 75:25). Thus, 0.2 g pure product of formula (III) were obtained, wherein X is 5-methyl furan-2-yl and Z is phenyl.

Rf = 0.60

$\lambda_{max} = 427$ nm ($E_1$ $_{cm}$$^{1\%}$ = 132.6).

EXAMPLE 19

In a solution of 5 g 3-o-toluidino-rifamycin S in 50 ml tetrahydrofuran, ammonia was bubbled at 6° C. for 10 minutes. The reaction mixture was allowed to stand overnight at room temperature. Under vacuum excess ammonia was removed, then adding under stirring 1 g powder zinc and 2 ml 5,6-dihydro-2H-pyran-3-aldehyde, followed by dropwise addition of 10 ml acetic acid at 10° C. Stirring was continued overnight at room temperature, the mixture was filtered and the filtrate treated as in the preceding examples to obtain 4.7 g raw product that chromatographied on silica gel column yielded 0.8 g product of formula (III), wherein X is 5,6-dihydro-2H-pyran-2-yl and Z is 2-tolyl.

Rf = 0.68

I.R. 3450, 3300, 1735(Sh), 1715, 1655, 1605(Sh), 1595, 1525, 1340, 1265, 1240, 1165, 1110, 1060, 1045(Sh), 1020, 970, 947, 918, 890, 870 and 805 cm$^{-1}$.

$\lambda_{max} = 259$ nm ($E_1$ $_{cm}$$^{1\%}$ = 296), 307 nm ($E_1$ $_{cm}$$^{1\%}$ = 337), 300 nm ($E_1$ $_{cm}$$^{1\%}$ = 92), 418 nm ($E_1$ $_{cm}$$^{1\%}$ = 134).

EXAMPLE 20

4 g 3-cyclopropylamino-4-desoxo-4-imino rifamycin S were dissolved in 50 ml tetrahydrofuran. The solution was cooled to 8° C. and added with 2 g powder zinc and 2 ml acetaldehyde, then followed by dropwise addition of 5 ml acetic acid under stirring. The mixture temperature was allowed to rise to room temperature, and after 2 hours the reaction was completed. The reaction mixture was filtered and treated as in the preceding examples to obtain a raw product that was purified by chromatography on column, obtaining 2.2 g yellow crystalline product of formula (III), wherein X is methyl and Z is cyclopropyl.

Rf = 0.52

I.R. 3150(B), 1740, 1720(Sh), 1665(Sh), 1650, 1600, 1560, 1520, 1340, 1310, 1240, 1160, 1145(Sh), 1085, 1060, 1040, 1020, 970, 940, 885, 850 and 805 cm$^{-1}$.

$\lambda_{max} = 223$ nm ($E_1$ $_{cm}$$^{1\%}$ = 494), 247 nm ($E_1$ $_{cm}$$^{1\%}$ = 361), 300 nm ($E_1$ $_{cm}$$^{1\%}$ = 328), 413 nm ($E_1$ $_{cm}$$^{1\%}$ = 216).

EXAMPLE 21

3 g 3-cyclopropylamino-4-desoxo-4-imino-rifamycin S were dissolved in 50 ml tetrahydrofuran. The solution was cooled to 10° C. and added with 1 g powder zinc and 3 ml 4-methoxy benzaldehyde, followed by dropwise addition of 5 ml acetic acid under stirring. The solution temperature was allowed to rise to room temperature and filtered after reacting for 5 hours. The filtrate was treated as in the preceding examples and after chromatography on column as previously described, 1.1 g yellow crystalline product of formula (III) was obtained, wherein X is 4-methoxy-phenyl and Z is cyclopropyl.

Rf = 0.61

I.R. 3400(B), 1735, 1715, 1655, 1605, 1560(Sh), 1515(Sh), 1510, 1340, 1305, 1260, 1240, 1180, 1155, 1115, 1060, 1025, 970, 940, 885, 835 and 800 cm$^{-1}$.

$\lambda_{max} = 271$ nm ($E_1$ $_{cm}$$^{1\%}$ = 287), 313 nm ($E_1$ $_{cm}$$^{1\%}$ = 428), 366 nm ($E_1$ $_{cm}$$^{1\%}$ = 128), 425 nm ($E_1$ $_{cm}$$^{1\%}$ = 145).

EXAMPLE 22

1 g 3-anilino-4-desoxo-4-imino-rifamycin S were dissolved in 10 ml tetrahydrofuran. Under stirring, 1 g powder zinc, 1 ml hexanal and 15 ml acetic acid were added. After stirring at room temperature for 15 minutes, excess zinc was filtered. The filtrate was treated as previously described obtaining a raw residue that was purified on column containing 30 g silica gel and eluting with a mixture benzene/acetone (8:2), finally obtaining 0.3 g yellow amorfous product of formula (III), wherein X is pentyl and Z is phenyl.

Rf=0.63

$\lambda_{max}$=413 nm ($E_1$ $_{cm}{}^{1\%}$=191).

EXAMPLE 23

3 g 3-cyclopropylamino-4-desoxo-4-imino-rifamycin S dissolved in 50 ml tetrahydrofuran were reacted overnight at room temperature with 3 ml cyclohexen-3-carboxyaldehyde in the presence of 2 g powder iron and 10 ml formic acid. The insoluble was filtered, the filtrate was added with 10% aqueous solution of sodium sulphite and extracted with chloroform. As dried and evaporated to dryness under vacuum, the organic layer yielded an amorphous solid that crystallized from benzene to give 1.7 g yellow crystalline product of formula (III), wherein X is 3-cyclohexene and Z is cyclopropyl.

The same product was obtained by using 1,4-dioxane and dimethyl sulphoxide as solvent.

Rf=0.62

I.R. 3300, 1725, 1660, 1605(Sh), 1590, 1542, 1520, 1335, 1255, 1228, 1170, 1070, 1050, 980, 950, 890, 860 and 805 cm$^{-1}$;

$\lambda_{max}$=225 nm ($E_1$ $_{cm}{}^{1\%}$=486), 251 nm ($E_1$ $_{cm}{}^{1\%}$=351), 300 nm ($E_1$ $_{cm}{}^{1\%}$=334), 416 nm ($E_1$ $_{cm}{}^{1\%}$=197).

What we claim is:

1. A rifamycin compound of the formula

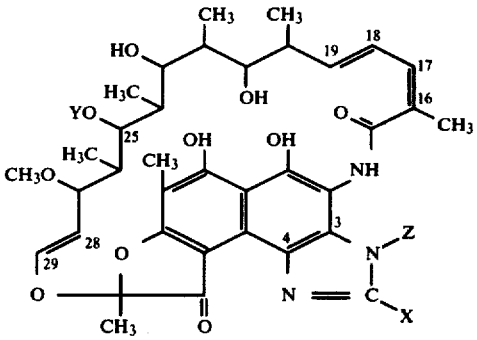

and 16, 17, 18, 19 tetrahydro derivatives and 16, 17, 18, 19, 28, 29 hexahydro derivatives thereof, wherein:

Y is —H or —COCH$_3$;

Z is an alkyl having 1–4 carbon atoms, cycloalkyl having 3–6 carbon atoms, phenyl, phenyl substituted with at least one radical selected from the group consisting of halogen, methyl, and hydroxy;

X is selected from the group consisting of hydrogen, alkyl having 1–5 carbon atoms, carboxy, formyl, phenyl, aromatic hydrocarbonalkenyl having 8 carbon atoms, cycloalkyl having 6 carbon atoms, cycloalkenyl having 6 carbon atoms, alkenyl having 3 carbon atoms, a heterocyclo selected from the group consisting of thienyl, furyl, pyridyl and 5,6-dihydro-2H-pyranyl, and substitution products of the above specified radicals having 1 or 2 radicals different therefrom and selected from the group consisting of halogen, methyl, methoxyl, N,N-dimethylamino and carboxyl.

* * * * *